United States Patent [19]

Meilland

[11] Patent Number: Plant 7,278

[45] Date of Patent: Jul. 24, 1990

[54] ROSE PLANT — MEIMAFRIS VARIETY

[75] Inventor: Marie-Louise Meilland, late of Antibes, France, by Jean-Pierre Le Naour, legal representative

[73] Assignee: The Conard-Pyle Company, West Grove, Pa.

[21] Appl. No.: 321,145

[22] Filed: Mar. 9, 1989

[51] Int. Cl.[5] ..... A01H 5/00

[52] U.S. Cl. ..... Plt./14

[58] Field of Search ..... Plt./14, 15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms abundantly and continuously attractive very double cream white blossoms which possess a long life. The plant exhibits a vigorous, compact, and bushy growth habit and is well adapted for growing in containers. The blossoms exhibit a particularly strong fragrance. The plant is well suited for growing in parks and gardens and is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Queen Elizabeth variety (U.S. Plant Pat. No. 1,259) by the Eleg variety (non-patented in the United States). The male parent (i.e., the pollen parent) was the Meidragelac variety (non-patented in the United States). The parentage of the new variety can be summarized as follows:

[Queen Elizabeth × Eleg] × Meidragelac.

The seeds resulting from the above pollination were sown and 95 plantlets were obtained which were physically and biologically different from each other. Selective study resulted in the identification of a single plant of the new variety.

It was found that the new variety of Hybrid Tea rose plant of the present invention possesses the following combination of characteristics:

(a) forms in abundance very double long lasting cream white blossoms which exhibit a strong fragrance,
(b) exhibits an upright, vigorous, compact and bushy growth habit,
(c) is well adapted for growing in containers, and
(d) is not particularly affected by cryptogamic diseases.

The exhibition of a strong blossom fragrance is considered to be most unusual in rose plants of this general blossom coloration.

The new variety well meets the needs of the horticultural industry since the plant blossoms continuously and abundantly. It is well adapted for growing and sale in containers, and is particularly suited for serving as an attractive decoration in parks and gardens.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meimafris variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelii* understock and growing outdoors at LeCannet des Maures, Var, France.

DETAILED DESCRIPTION

Figures 1, 2, 3, 4, 5, 6, 7, 8, 9, 10, 11, 12, 13, 14, 15, 16:
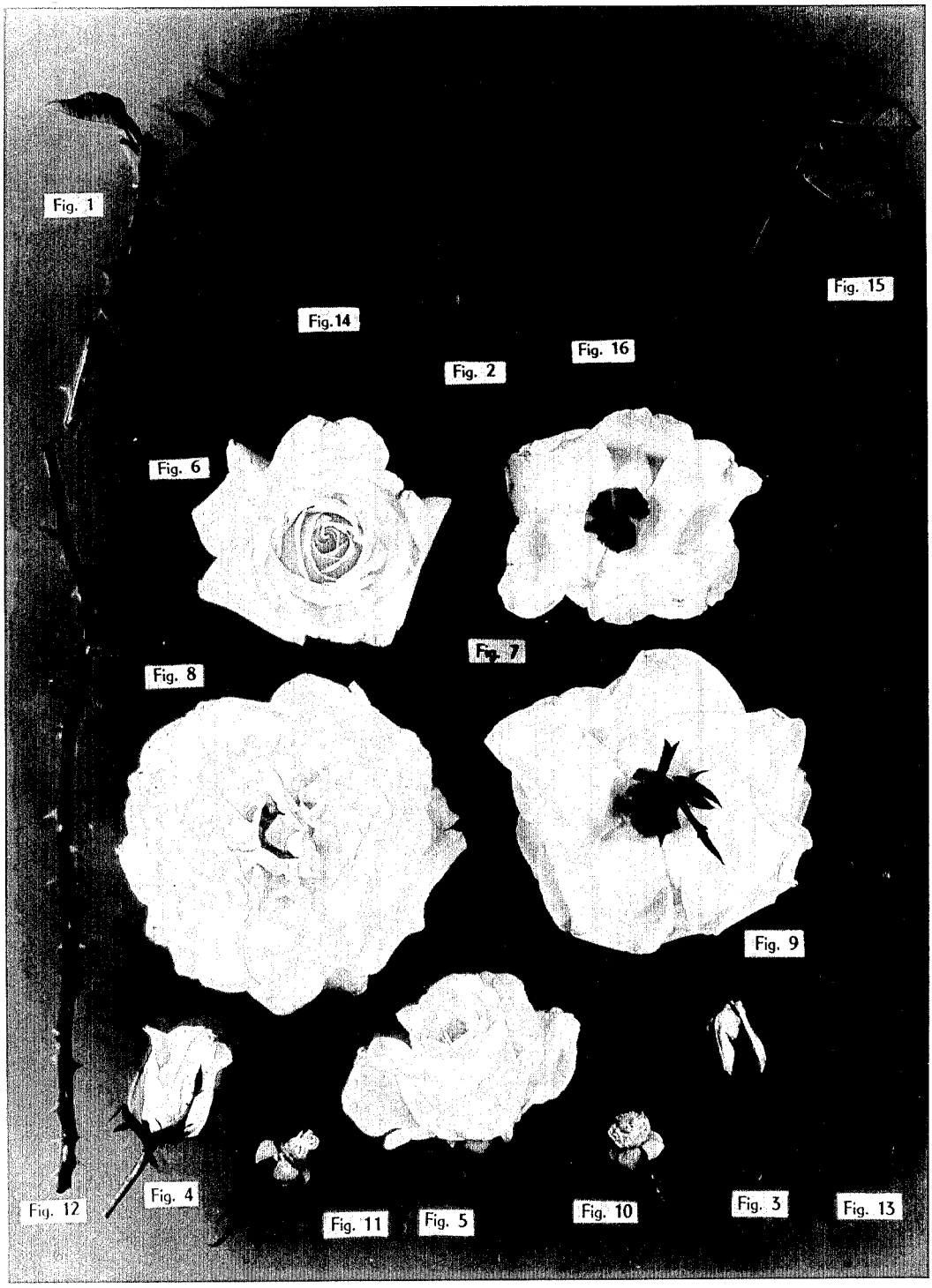
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of an adult branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that The Royal Horticultural Society (R.H.S. Colour Chart). The description is based on two year old plants made during June while budded on *Rosa froebelii* understock and growing outdoors at LeCannet des Maures, Var, France. The coloration in common terms precedes reference to the chart.

Class: Hybrid Tea.

Plant:

*Height.*—Approximately 90 to 120 cm.

*Habit.*—Upright.

Branches:

*Color.*—Young stems: light green, Yellow-Green Group 146C, tinted with reddish green. Adult wood: medium green, Yellow-Green Group 146B.

*Thorns.*—Size: medium to large. Quantity: Numerous. Color: Pinkish on young canes and brown on adult canes.

Leaves:

*Stipules.*—Adnate, pectinate, very wide and linear.

*Petioles.*—Upper surface: striped, reddish brown on young leaves and medium green on adult foliage with glandular edges. Under surface: light green, and bear some thorns.

*Leaflets.*—Number: 3, 5, and 7 (most often). Shape: oval Serration: simple and regular. Texture: leathery. General appearance: dense and semi-dull. Color (young foliage): Upper surface: reddish brown. Under surface: reddish brown. Color (adult foliage): Upper surface: dark green, Yellow-Green Group 147A. Under surface: medium green, Yellow-Green Group 147B.

Inflorescence:

*Number of flowers.*—Generally 1 to 5 per stem.

*Peduncle.*—Straight, rigid, more or less tinted reddish brown, and commonly bear a few thorns and pediculate glands. The length is approximately 5 cm. on average.

*Sepals.*—Upper surface: tomentose, greenish and slightly tinted reddish in coloration. Under surface: smooth, light green in coloration, the edges of the outer sepals are slightly appendiculated.

*Buds.*—Shape: Elongated. Length: approximately 4 cm. on average. Size: average. Color upon opening: Upper surface: cream white, Yellow-White Group 158B, with slightly rosy edges. Under surface: cream white, Yellow-White Group 158B with slightly pinkish edges.

*Flower.*—Shape: cup-like and very double. Diameter: approximately 12 cm. on average. Color (when opening begins): Upper surface: cream white, Yellow-White Group 158B and tinted with light orient pink, Red Group 36C, and light Naples yellow, Yellow Group 11C, at the base of the petals. Under surface: same as upper surface. Color: (when blooming): Upper surface: light cream white, Yellow-White Group 158D, and slightly tinted with light orient pink, Red Group 36D, and light amber yellow, Yellow-Orange Group 18C, at the base of the inner petals. Under surface: same as upper surface. Color (at end of opening): Upper surface: pale cream white, Yellow-White Group 158D, and slightly tinted with pale orient pink, Red Group 36D. Under surface: same as upper surface. Fragrance: Strong. Lasting quality: long. Petal number: approximately 65 on average. Petal form: oval. Texture: consistent. Petal drop: the petals drop off cleanly. Stamen number: approximately 102 on average. Anthers: yellow in coloration. Filaments: orange-yellow in coloration, of irregular heights. Pistils: approximately 56 on average. Stigmas: normal, yellowish in coloration, located above the anthers. Styles: fuchsine in coloration, often bonded together at base, and of irregular heights. Receptacle: light green, smooth, in longitudinal section are wide and in the shape of a funnel.

Development:

*Vegetation.*—Vigorous.

*Blooming.*—Abundant and continuous.

*Aptitude to bear fruits.*—Normal.

*Resistance to diseases.*—Good.

*Resistance to frost.*—Good.

I claim:

1. A new and distinct variety of Hybrid Tea rose plant characterized by the following combination of characteristics:

(a) forms in abundance very double long lasting cream white blossoms which exhibit a strong fragrance, (b) exhibits an upright, vigorous, compact and bushy growth habit, (c) is well adapted for growing in containers, and (d) is not particularly affected by cryptogamic diseases; substantially as herein shown and described.

* * * * *